United States Patent [19]

Tamura et al.

[11] Patent Number: 5,196,898
[45] Date of Patent: Mar. 23, 1993

[54] OPTICAL LIQUID SENSOR, A METHOD OF MANUFACTURING THE SAME, AND AN AUTOMOTIVE OIL/BATTERY CHECKER EMPLOYING THE SENSOR

[75] Inventors: Kunimitsu Tamura, Warabi; Taizo Takatori, Kitakatsuragi; Akihiro Ishihara, Nara; Tadaaki Masui, Osaka, all of Japan

[73] Assignee: Tatsuta Electric Wire and Cable Co., Ltd., Osaka, Japan

[21] Appl. No.: 601,777

[22] PCT Filed: Apr. 24, 1990

[86] PCT No.: PCT/JP90/00531
§ 371 Date: Nov. 29, 1990
§ 102(e) Date: Nov. 29, 1990

[87] PCT Pub. No.: WO90/13018
PCT Pub. Date: Nov. 1, 1990

[30] Foreign Application Priority Data

| Mar. 27, 1989 | [JP] | Japan | 2-32642 |
| Apr. 25, 1989 | [JP] | Japan | 1-49135 |
| Jun. 27, 1989 | [JP] | Japan | 1-75072 |
| Nov. 28, 1989 | [JP] | Japan | 1-137651 |
| Dec. 22, 1989 | [JP] | Japan | 1-148091 |
| Mar. 26, 1990 | [JP] | Japan | 2-31745 |
| Mar. 28, 1990 | [JP] | Japan | 2-79944 |

[51] Int. Cl.⁵ .................... G01N 33/28; G01N 21/88; G01N 21/59
[52] U.S. Cl. .................... 356/70; 250/576; 324/157; 356/72; 356/440
[58] Field of Search ............ 356/70, 72, 436, 440, 356/250; 250/573, 576; 324/426, 149, 157

[56] References Cited
U.S. PATENT DOCUMENTS

| 2,889,736 | 6/1959 | Borg | 250/576 X |
| 4,893,935 | 1/1990 | Mandel et al. | 356/436 |
| 4,989,942 | 2/1991 | Koenigsberg et al. | 356/436 |

FOREIGN PATENT DOCUMENTS 60-201238 10/1985 Japan ..................... 356/70

Primary Examiner—Vincent P. McGraw
Attorney, Agent, or Firm—Jordan and Hamburg

[57] ABSTRACT

An optical liquid sensor comprises an optical fiber folded back in two, a light-emitting element disposed at one end of the optical fiber, a light-receiving element disposed at the other end, and a detection means comprising a pair of units of a rod lens and/or large-diameter glass optical fiber with a narrow gap interposed therebetween in a linear segment of a folded-back portion of the optical fiber, the folded-back portion being hermetically sealed except at an aperture portion for admitting a liquid into the narrow gap. In this sensor, the loss of light at the narrow gap is minimized. In the manufacture of the sensor, a special jig is used for insuring that a rod lens or the like is accommodated in a metal sheath in such a manner that its forward end is flush with the end face of the sheath or projects slightly beyond the end face. Furthermore, by using the above sensor, there is provided an on oil/battery checker which can be used for determination of the degree of degradation of engine oil and detection of the charge voltage of a car battery.

13 Claims, 10 Drawing Sheets

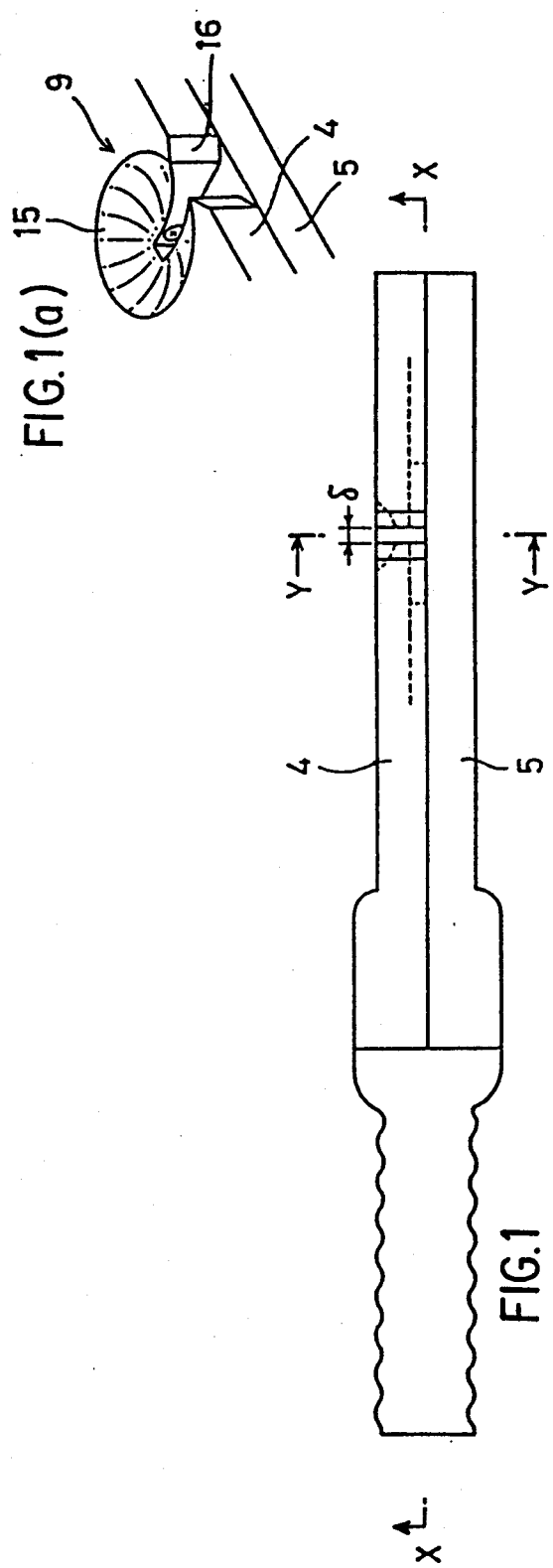
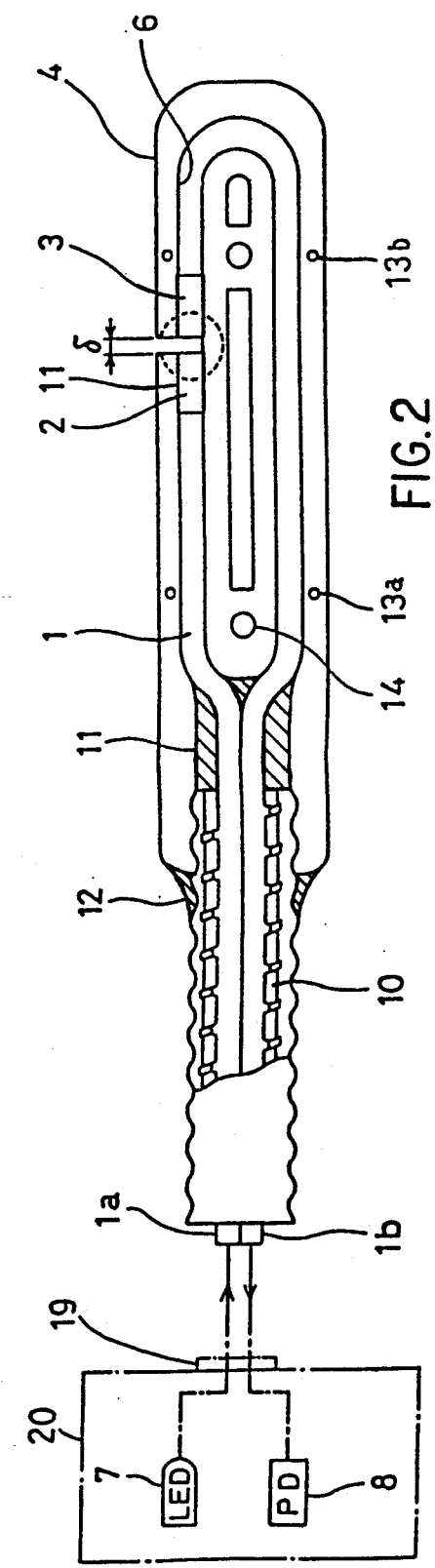
FIG.1(a)
FIG.1
FIG.2

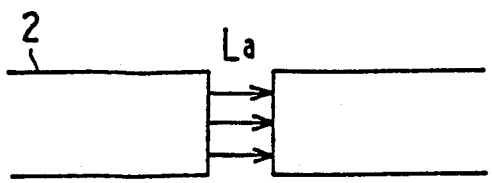
FIG 8(a)
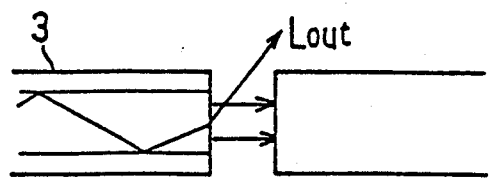
FIG.8(c)
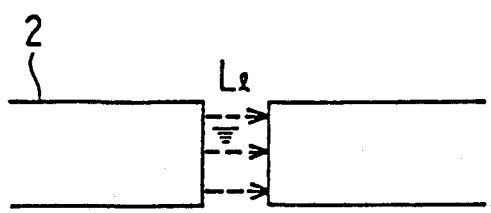
FIG.8(b)
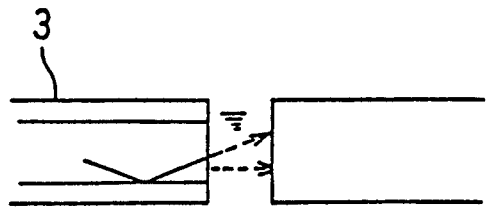
FIG.8(d)
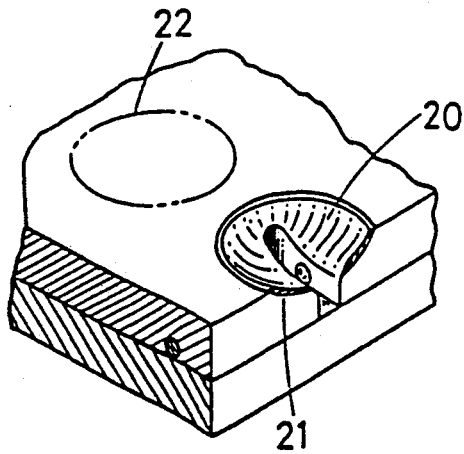
FIG.9(a)
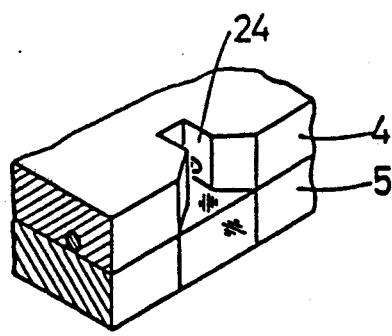
FIG.9(b)
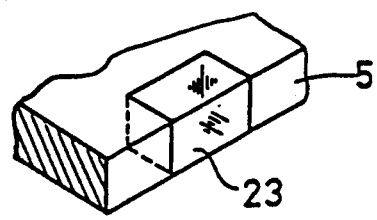
FIG.9(b')

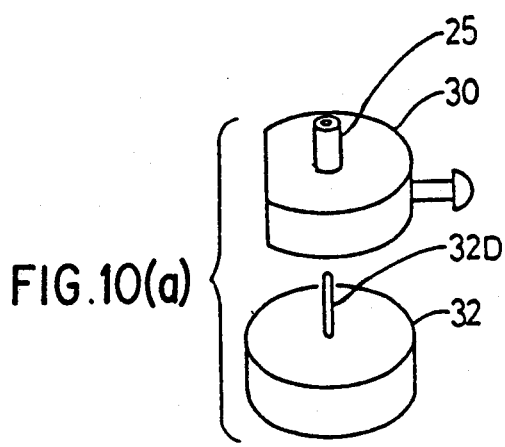
FIG.10(a)
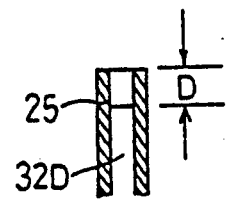
FIG.10(b')
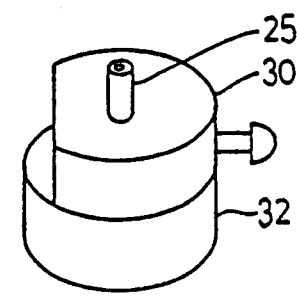
FIG.10(b)
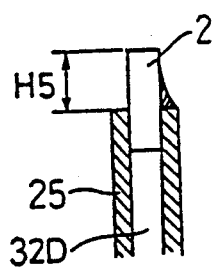
FIG.10(c')
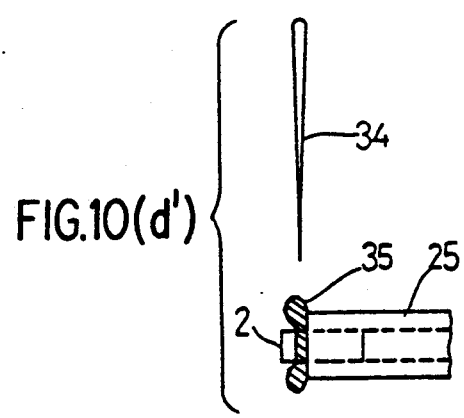
FIG.10(d')
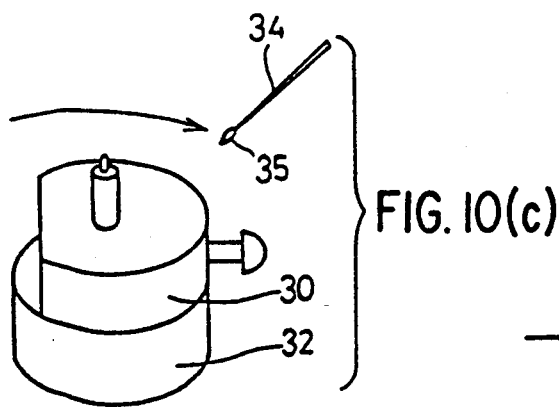
FIG.10(c)
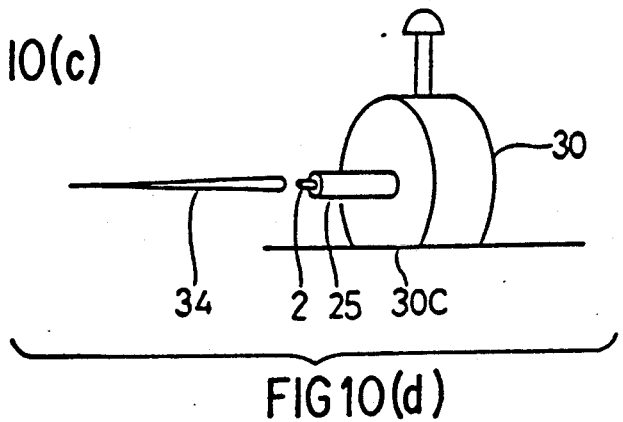
FIG 10(d)

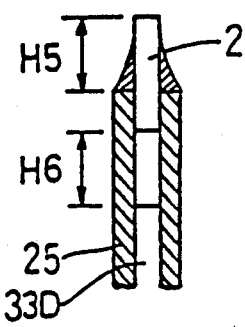
FIG.11(d')
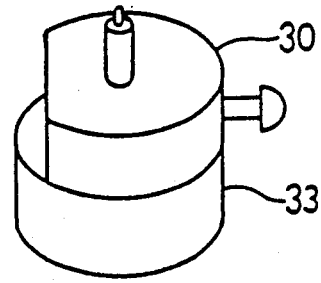
FIG.11(a)
FIG.11(b')
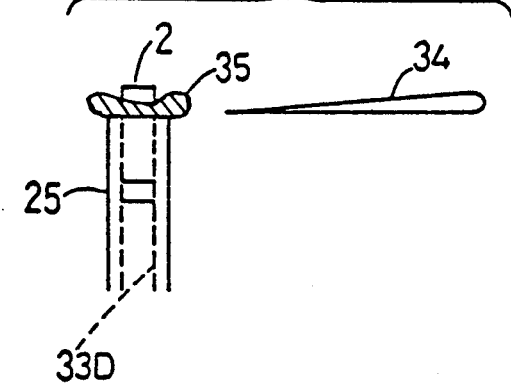
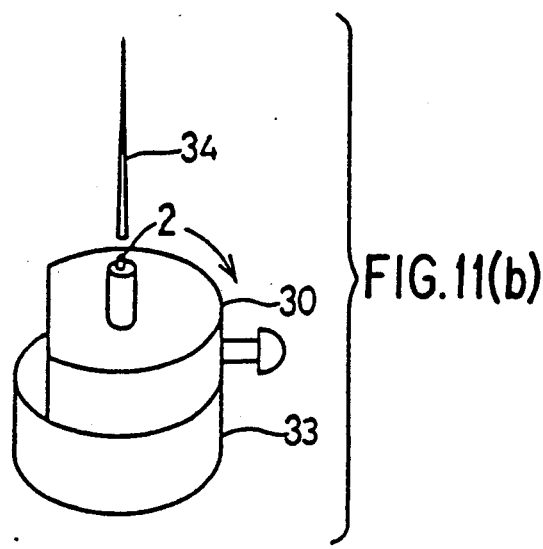
FIG.11(b)

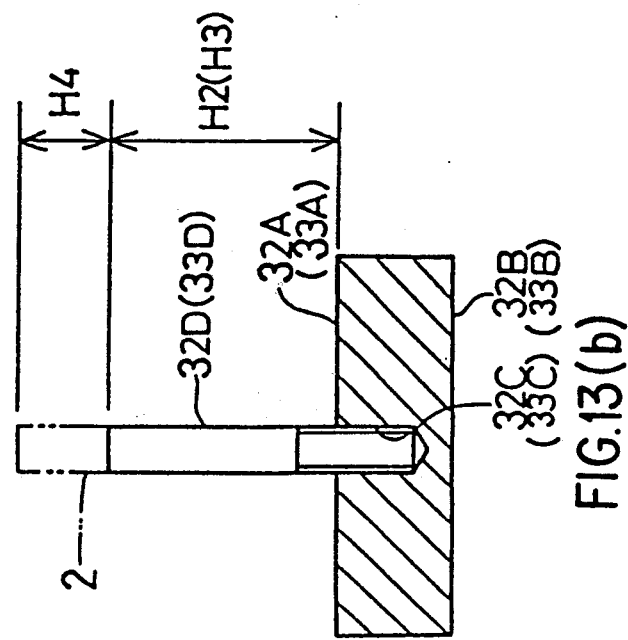
FIG.13(a)
FIG.13(b)
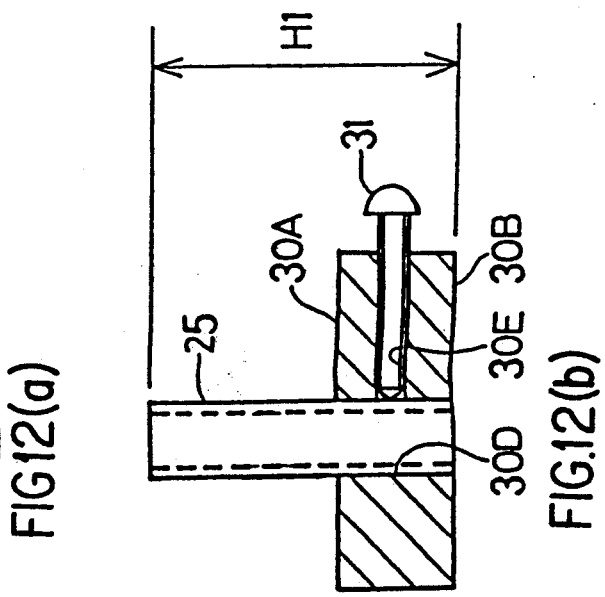
FIG.12(a)
FIG.12(b)

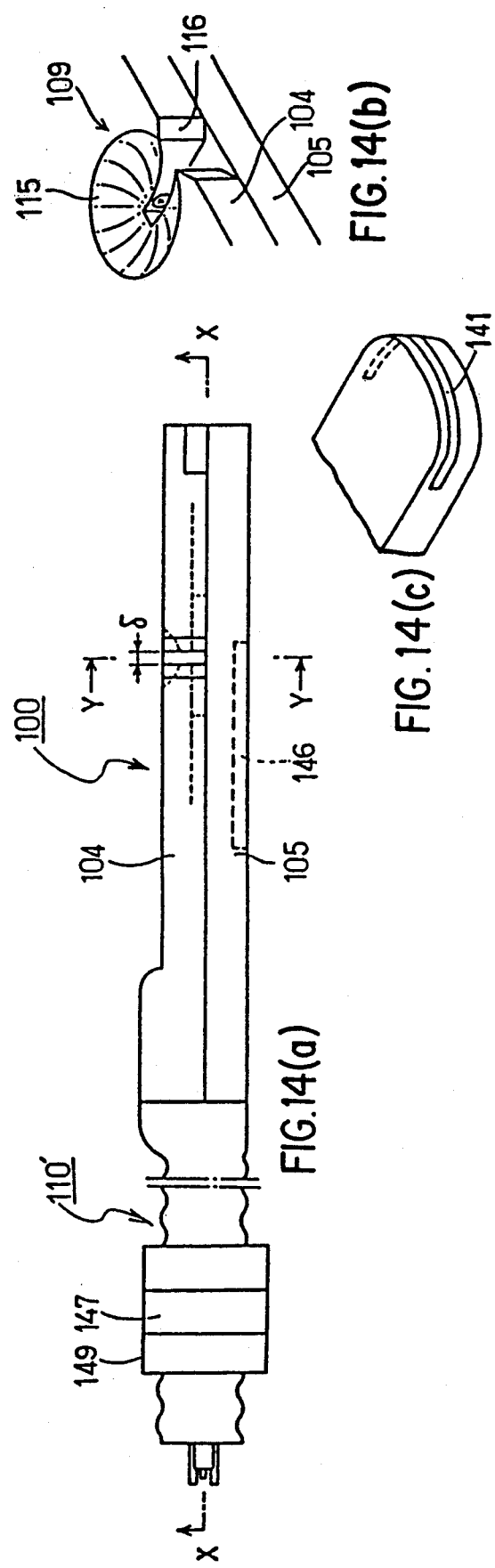
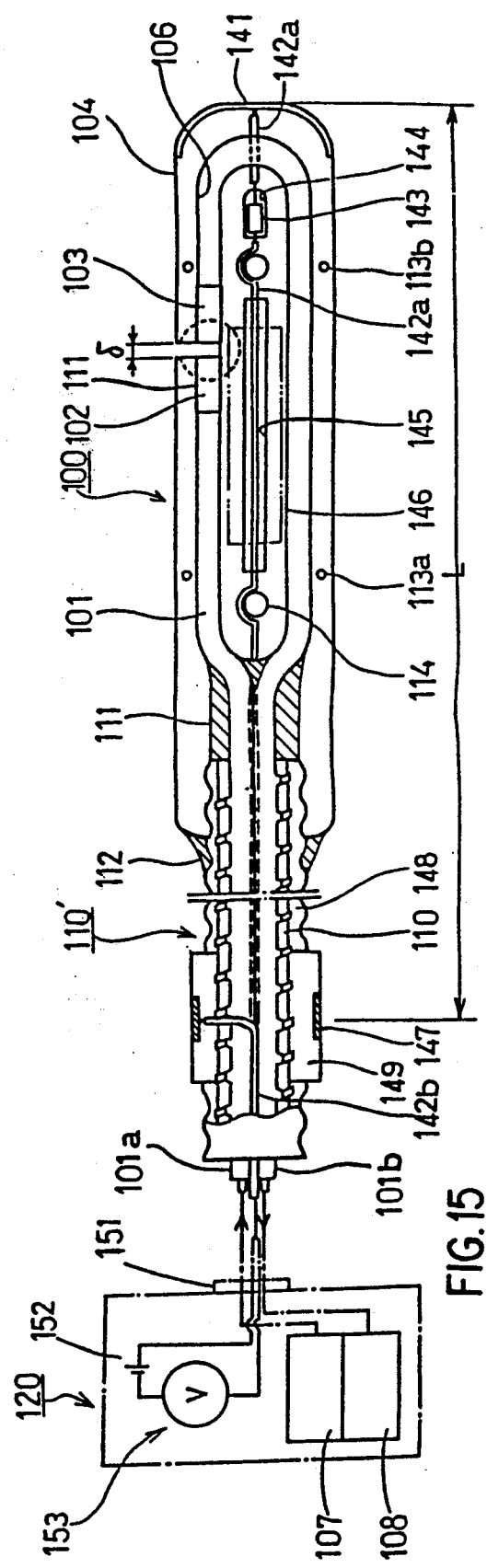

OPTICAL LIQUID SENSOR, A METHOD OF MANUFACTURING THE SAME, AND AN AUTOMOTIVE OIL/BATTERY CHECKER EMPLOYING THE SENSOR

TECHNICAL FIELD

The present invention relates to an optical liquid sensor adapted to measure the degree of degradation or contamination of engine oil, frying oil, water, ink or the like o the concentration of a liquid such as coffee, tea, etc. according to the transmission loss of light, a method of manufacturing said sensor and an automotive oil/battery checker utilizing the same sensor.

BACKGROUND ART

The hitherto-known optical liquid sensor comprises a mirror and a beam splitter as illustrated in FIG. 19. Here, a light output 72 of a light-emitting element 71 passes through a beam splitter 73 (or a photocoupler) and an optical fiber 75 accommodated in a flexible duct 74 and reaches a detection means 76. The detection means 76 comprises said optical fiber 75 and a mirror 77 juxtaposed with an intervening gap $\epsilon$ which is to be filled up with a liquid substance to be tested (hereinafter referred to as the test liquid) A transmission loss of light attributable to the test liquid occurs in the course of travel of light 72 as it is reflected by the mirror 77 and returns to the optical fiber 75. A reflected light 78 returning to the optical fiber 75 is reflected by the beam splitter 73 and impinges on a light-receiving element 70, the output of which is amplified by an amplifier 80 for detection. This light output has been attenuated according to the transmission loss caused by the test liquid in the gap $\epsilon$ and the degree of contamination or the concentration of the liquid is determined from the degree of the above attenuation.

In the above optical liquid sensor employing a mirror and a beam splitter, reflection losses at the mirror 77 and beam splitter 73 are fairly large and the sensitivity of the system is as much decreased. Therefore, the use of a high-sensitivity amplifier 80 is essential. Moreover, an expensive beam splitter 73 is an absolute necessity. Thus, the initial cost of the system is high. Furthermore, in the system employing a mirror 77, the distance of travel of light is $2\times\epsilon$. Therefore, when the test liquid is one of large transmission loss, the gap $\epsilon$ must be so small that it is difficult to fill and remove the test liquid with respect to the gap $\epsilon$.

Having been accomplished to overcome the above-mentioned disadvantages, the present invention has as its object to provide an optical liquid sensor which is highly sensitive and provides ease of filling and removal of the test liquid.

It is another object of the present invention to provide a method of manufacturing such an optical liquid sensor.

A still another object is to provide an automotive oil/battery checker employing the sensor.

SUMMARY OF THE INVENTION

The optical liquid sensor of the present invention comprises a folded-back optical fiber, a light-emitting element disposed at one end of said optical fiber, a light-receiving element disposed at the other end, and a detection means wherein each rod lens and/or a large-diameter glass optical fiber forming a pair is accommodated in juxtaposition with a narrow gap interposed therebetween in a linear segment of a folded-back portion of said optical fiber, with said folded-back portion being hermetically sealed except at an aperture for admitting a liquid to be measured into said narrow gap.

Since the detection means is formed with a narrow gap interposed between two of said rod lens and/or large-diameter glass optical fiber forming the pair in a linear segment of said folded-back region, the loss of light at said narrow gap due to offset of the light path is minimized. Furthermore, the rod lens and/or large-diameter glass optical fiber is chemically stable against a variety of liquids to be measured and this stability also reduces chances for the occurrence of losses of light. Thus, when the rod lens is used, the transmission light through the narrow gap is collimated into a beam of parallel rays, while the large-diameter glass optical fiber offers a large light reception area with respect to said narrow gap, with the result that the loss of light is decreased. This effect of reduction in light loss is available in the case wherein a rod lens and a large-diameter glass optical fiber constitute said pair and in the case where either rod lenses or large-diameter glass optical fibers constitute said pair.

Since the structural chances of causing a light loss are thus reduced, the sensor according to the present invention insures a high sensitivity of determination despite its simple construction which lends itself well to manufacturing.

The detection means is preferably formed by inserting each rod lens or large-diameter glass optical fiber forming a pair into a metal sheath in such a manner that its forward end projects by 0 to 0.3 mm beyond the end face of said metal sheath with the other end abutted against the core of an optical fiber within said metal sheath, with the projecting ends of said pair being juxtaposed with said narrow gap $\delta$ interposed therebetween.

Since the rod lens and/or large-diameter glass optical fiber is abutted against the core of an optical fiber in a metal sheath in the above manner, the loss of light due to offset of the light path is minimized. Furthermore, since the forward end of said rod lens and/or large-diameter glass optical fiber is projecting by 0 to 0.3 mm, the drainage of said gap is facilitated and can be visually ascertained.

It is also preferable that the member sealing the folded-back region of said optical fiber be a light-opaque member and that said narrow gap be open on at least two of its four sides.

The sealing by such a light-opaque member precludes interference by external light. Moreover, since at least two of the four sides of said narrow gap are open, the filling and removal of the liquid are facilitated. Therefore, the invention provides an optical liquid sensor which insures a high accuracy of determination and is easy to use.

Furthermore, the aperture around said narrow gap is partially formed in a funnel-like configuration.

This configuration further facilitates filling and removal of the liquid.

The top surface of said detection means which is above said aperture for admitting the liquid to be measured or the area adjoining thereto is preferably made of a white material.

In this manner, by dripping engine oil or the like on said top surface or adjoining area above the aperture around said narrow gap at the same time as dripping it into said narrow gap, the degree of contamination of the engine oil can be clearly ascertained by visual inspection against the white background.

In lieu of the above arrangement, the part of said detection means which lies immediately under said aperture can be made of a light-transparent material such as glass.

In this case, the engine oil dripped into the narrow gap collects on top of the light-transparent member so that the degree of contamination of the engine oil can be visually confirmed by overhead inspection relying on the external light from below.

Thus, in the last mentioned two embodiments where the degree of contamination of the liquid to be measured is a subject of determination as it is the case with engine oil, not only a quantitative determination of the degree of contamination according to a change in concentration but a visual verification by the person requesting an inspection can be made feasible.

The present invention further provides a method of manufacturing an optical liquid sensor for measuring the degree of fouling or the like according to the transmission loss of light in the narrow gap defined by a juxtaposed pair of rod lenses or the like accommodated in a metal sheath.

An easily conceivable method for the manufacture of an optical liquid sensor of this type would be a manual method which comprises inserting a rod lens or large-diameter glass optical fiber coated with an adhesive composition around its periphery into a metal sheath or tube form one end thereof, removing the overflowing adhesive and fixing the rod lens or large-diameter glass optical fiber firmly in position where the leading end of said rod lens or large-diameter glass optical lens is flush with the end face of the metal sheath or projects slightly beyond said end face. In such manual method, however, the operation for applying the adhesive to the peripheral surface of the rod lens or large-diameter glass optical fiber becomes unstable and the coating result cannot be uniform because there is no means for the proper positioning of the rod lens or large-diameter glass optical fiber.

The present invention, in another aspect, provides a method of manufacturing an optical liquid sensor which is free from the above-mentioned disadvantages. The method of the present invention, thus, provides a method for manufacturing an optical liquid sensor such that a rod lens or a large-diameter glass optical fiber for forming a pair is accommodated in a metal sheath in such a manner that its forward end is flush with said metal sheath or projects slightly beyond the end face of said sheath with the other end abutted against the core of a plastic optical fiber within the metal sheath and a pair of units of such rod lens and/or large-diameter glass optical fiber are juxtaposed with a narrow gap interposed therebetween in said metal sheath, which method comprises providing a metal sheath holder having a disk member having a metal sheath insertion hole extending vertically therethrough and locking means for securing a metal sheath passed through said metal sheath insertion hole in position, passing a metal sheath through said metal sheath insertion hole and setting it in a position where one end thereof does not project beyond the underside of said disk, providing a platen and an adjusting jig having an adjusting rod extending vertically to a predetermined height above the top surface of said platen, passing said metal sheath as fixedly supported by said metal sheath holder over said adjusting rod, passing a rod lens or a large-diameter glass optical fiber into said metal sheath until its lower end is abutted against the tip of the adjusting rod of said adjusting jig, applying an adhesive to a portion of said rod lens or large-diameter glass optical fiber which is projecting beyond the end face of said metal sheath, withdrawing said adjusting jig and pushing in the rod lens or large-diameter glass optical fiber until its forward end is flush with the end face of said metal sheath or projects slightly beyond said end face, while the overflowing adhesive is removed so that it will not be deposited on the forward end face of said rod lens or large-diameter optical glass fiber, to provide an integral unit.

Since, the above method, the metal sheath fixedly supported by a metal sheath holder is passed over the adjusting rod of an adjusting jig and the rod lens or large-diameter glass optical fiber is then inserted until its lower end is abutted against the tip of the adjusting rod of said adjusting jig, the projecting length of the rod lens or large-diameter glass optical fiber relative to the metal sheath is kept constant and, moreover, because said lens or fiber is supported from below, the lens or fiber is not disturbed so that the adhesive composition can be easily and evenly applied. A greater uniformity of application of the adhesive is insured when the adhesive is applied while the metal sheath holder is rotated. As a consequence, the incidence of rejects due to formation of a raised mass of the cured adhesive and the consequent poor drainage of the narrow gap is minimized.

A preferred mode of the above method comprises providing, in addition to said first adjusting jig whose adjusting rod has a height insuring a projection length necessary for application of the adhesive, a second adjusting jig having an adjusting rod set to a length insuring that the forward end of said rod lens or large-diameter glass optical fiber is flush with the end face of said metal sheath or projects slightly beyond said end face, fixing said metal sheath as fixedly supported by said metal sheath holder to said first adjusting jig and applying an adhesive, then passing said metal sheath as fixedly supported by said metal sheath holder to said second adjusting jig, and pushing in said rod lens or large-diameter glass optical fiber until its lower end is abutted against the tip of the adjusting rod of said second adjusting jig while the overflowing adhesive is removed so that it is not deposited on the forward end face of said lens or fiber.

By using the second adjusting rod described above, the rod lens or large-diameter glass optical fiber can be uniformly finished within good tolerances when the end face of said rod fiber or glass optical fiber is flush with the end face of said metal sheath or projects slightly beyond said end face. Therefore, the incidence of rejects due to poor drainage which interferes with visual evaluation is minimized.

The optical liquid sensor described above can be utilized in an automotive oil/battery checker to be used at a filling station for determination of the degree of contamination of engine oil and the detection of battery charge voltage.

Filling stations in Japan as well as in other countries offer services including car washing and simple repairing in addition to gas filling. Recently, there has been a demand for rapid, expedient and accurate checks of the degree of degradation of engine oil and of battery charge voltage during the filling time.

In such servicing, the optical liquid sensor described above can be used for the check of the degree of degradation of engine oil together with a commercial voltmeter for the checking of battery charge voltage. However, since such optical liquid sensor and voltmeter are independent measuring devices, it takes time to operate these independent devices during the short filling time.

This disadvantage is overcome by the present invention which provides an automotive oil/battery checker by which both the detection of the degree of degradation of engine oil and the detection of battery charge voltage can be carried out in a short time. This automotive oil/battery checker comprises a sensor head comprising a folded-back light transmission path which is hermetically closed except for a narrow gap provided in one location in the folded-back portion of said path for admitting an oil to be tested for contamination and one terminal disposed on the surface thereof for detecting a battery charge voltage, a flexible conduit disposed adjacent said sensor head and covering both an outward segment and an inward segment of said light transmission path, having another terminal disposed on the surface thereof for detecting a battery charge voltage, and further covering lead wires connected to said two terminals, and a measuring unit disposed at a terminal end of said flexible conduit and having a light loss detector having a light emission means and a light reception means and a voltmeter connected to said two terminals through lead wires, the distance between one of said terminals which is disposed on said sensor head and the other terminal disposed on said flexible conduit being larger than the distance between two power terminals of a battery and being adjustable in response to flexure of said flexible conduit, whereby both the detection of the degree of degradation of engine oil and the detection of battery charge voltage can be effected.

In the above automotive oil/battery checker, the sensor head is provided with both the narrow gap for detecting the degradation of oil and one terminal for detection of battery charge voltage, the other terminal for detection of battery charge voltage is disposed in the flexible conduit and the measuring unit includes a light loss measuring device and a voltmeter, so that both the determination of the degree of degradation of engine oil and the detection of battery charge voltage can be accomplished with a single measuring instrument. Therefore, the quality of filling and other services can be improved by performing both of the above determination and detection in a continuous flow and quickly.

Preferably, a magnetic plate is flush-mounted on the surface of the sensor head in a position opposite to the aperture for admitting engine oil into said narrow gap.

In this arrangement, the oil check can be expedited by letting the sensor head attach itself to a suitable flat surface in the engine compartment by taking advantage of the attraction force of said magnetic plate and dripping the oil with one hand while the checker is manipulated with the other hand.

Furthermore, just as in the case of the optical liquid sensor described hereinbefore, the following arrangements are preferably adopted.

1. The narrow gap mentioned above is formed by inserting each rod lens or large diameter glass optical fiber forming a pair into a metal sheath in such a manner that its forward end projects by 0 to 0.3 mm beyond the end face of the metal sheath with the other end being abutted against the core of an optical fiber in said metal sheath so that two projecting ends of the pair are juxtaposed in said metal sheath.

2. The covering member sealing the folded-back portion is made of a light-opaque material and the aperture for admitting engine oil is open on at least two of its four sides.

3. The aperture portion around said narrow gap is partially formed in a funnel-like configuration.

4. The top surface of the aperture portion for admitting oil into said narrow gap is comprised of a white member.

5. The member under said aperture for admitting oil into said narrow gap is comprised of a light-transparent material such as glass.

BRIEF DESCRIPTION OF THE DRAWINGS

FIG. 1 is a side-elevation view showing an optical liquid sensor and FIG. 1(a) is an enlarged perspective view of a detail thereof;

FIG. 2 is a sectional view taken along the line X—X of FIG. 1;

FIGS. 8(a-d) are diagrams showing the transmission loss of light in optical liquid sensors;

FIGS. 9(a-b') are perspective views showing other examples of the aperture for admitting the test liquid;

FIGS. 10(a-d') and 11(a,b') are respective sets of diagrams showing respective manufacturing processes for the optical liquid sensor;

FIGS. 12(a,b) are views showing the metal sheath holder to be used in said manufacturing process;

FIGS. 13(a,b) are views showing a first and a second adjusting jig to be used in said manufacturing process;

FIG. 14(a) is a side-elevation view showing an automotive oil/battery checker and FIGS. 14(b) and 14(c) are perspective views of details thereof;

FIG. 15 is a sectional view taken along the line X—X of FIG. 14;

DETAILED DESCRIPTION OF PREFERRED EMBODIMENTS OF THE INVENTION

Figure 3:
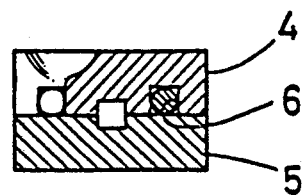
FIG. 3 is a sectional view taken along the line Y—Y of FIG. 1.

Referring to FIGS. 1 and 1A through 3, the optical liquid sensor comprises a folded-back plastic optical fiber 1, a rod lens 2, which may for example be a self-focusing lens, and a large-diameter glass optical fiber 3 juxtaposed to the rod lens 2 with a narrow gap δ interposed therebetween, and a pair of top and bottom cover plates 4, 5 adapted to sealingly cover the above-mentioned members as a unit.

The top cover plate 4 is provided with an elongated annular groove 6 and said narrow gap δ is formed in a linear portion of said groove 6. The plastic optical fiber 1 is accommodated in the folded-back manner in said groove 6. Also disposed in the groove 6, on respective sides of said narrow gap δ, is said rod lens 2, which is connected to a plastic optical fiber 1a extending from a light-emitting element 7, and said large-diameter glass optical fiber 3, which is connected to a plastic optical fiber 1b extending to a light-receiving element 8. The rod lens 2 and the large-diameter glass optical fiber 3 juxtaposed thereto with the narrow gap δ interposed therebetween constitutes a detection means 9. The fitting portions of the rod lens 2 and large-diameter glass optical fiber 3 and the inlet end of the plastic optical fiber 1 into a metallic flexible conduit 10 are sealed with an adhesive coating composition 11. The metallic flexible conduit 10 is covered with a cladding and the gap between this conduit 10 and the top protective cover plate 4 is also sealed up with an adhesive layer 12.

The bottom protective cover plate 5 is configured as a flat member and is set in position with respect to the top protective cover plate 4 as its side holes and projections (not shown) are engaged with corresponding projections 13a and holes 13b, respectively, of the top cover plate 4 and secured there with bolts threaded into bolt holes 14. An adhesive composition is further applied between the mating surfaces of said bottom protective cover plate 5 and top protective cover plate 4 to hermetically seal the rod lens 2, large-diameter glass optical fiber 3 and plastic optical fiber 1.

The detection means 9 having said narrow gap δ is configured, as illustrated in FIGS. 1(a), to provide an aperture which is open at the top and near lateral sides and closed on the bottom and far lateral sides. The top opening is configured like a funnel as indicated at 15, with the center of the funnel 15 being situated in the position opposing the rod lens 2 and large-diameter glass optical fiber 3. The near lateral side of said aperture is recessed to form chamferred portions 16. The bottom protective cover plate 5 and top protective cover plate 4 are formed of a light-opaque material such as a black polycarbonate resin so as to minimize the infiltration of unwanted light into the detection means 9 where the rod lens 2 and the large-diameter glass optical fiber are juxtaposed. In the detection means 9 thus configured, the test liquid dripped into the funnel-shaped aperture 15 fills up the narrow gap δ due to its surface tension. After determination, the test liquid can be easily removed from the narrow gap δ, for example by blasting a breath against the liquid from between the chamferred portions 16 of the aperture.

Figure 4A:
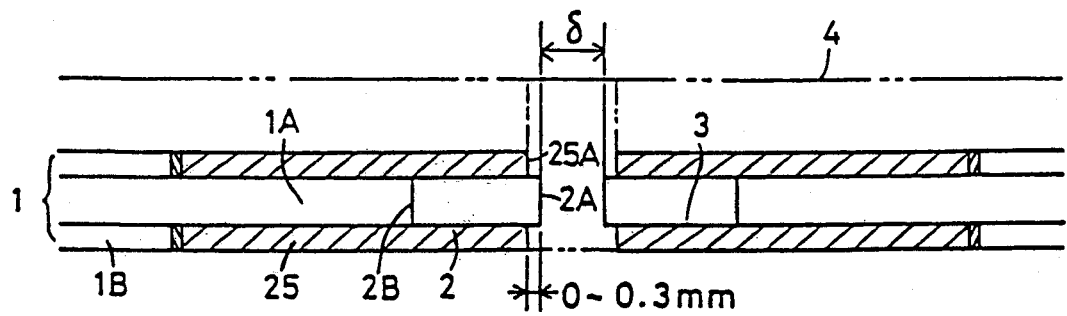
FIGS. 4(a-e) are diagrammatic views showing detection means.

While the rod lens 2 is directly fitted in the groove 6 as shown in FIG. 2, it is preferably installed in position through a metal sheath 25 as illustrated in FIG. 4(a). In this case, the rod lens 2 is inserted into the metal sheath 25 with constant application of an adhesive composition and its tip, indicated at 2A, projecting from the sheath by 0 to about 0.3 mm. When the distance of projection is 0 mm, the end face 25A of the metal sheath is flush with the forward end 2A of the rod lens. And the core 1A of the plastic optical fiber bared of its cladding 1B is inserted into the metal sheath 25 until the forward end of the core 1A is abutted against the other end 2B of the rod lens in the metal sheath 25. As the rod lens 2 and the core 1A of the optical fiber are abutted against each other within the metal sheath 25, the light axes of the two members are accurately lined up so that the loss of light due to offset is minimized. In this manner the optical liquid sensor can be easily manufactured with good dimensional reproducibility.

Figure 4B:
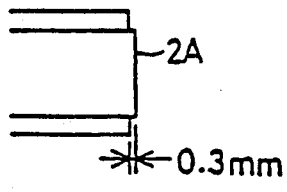
Figure 4C:
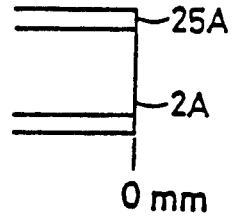
Figure 4D:
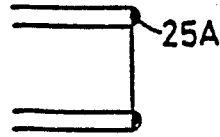
Figure 4E:
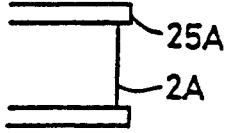
Figure 4F:
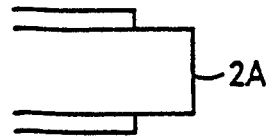

The projecting distance of 0 to 0.3 mm at the forward end 2A of the rod lens is further explained below. When the forward end 2A of the rod lens is projecting slightly as illustrated in FIG. 4(b), the drainage of the test liquid, such as oil, at the end 2A is facilitated and can be readily ascertained by the naked eye. In contrast, when the end 2A of the rod lens is projecting beyond 0.3 mm, the drainage of the test liquid at the lateral sides of the projecting end is adversely affected. The drainage of the test liquid is fairly good and can be visually confirmed rather easily when the end 2A of the rod lens and the forward end 25A of the metal sheath are flush as shown in FIG. 4(c). However, the drainage is poor when the adhesive is raised in the shape of a ring on the end 25A of the metal sheath as illustrated in FIG. 4(d) or the end 25A of the metal sheath is projecting farther than the rod lens 2A as illustrated in FIG. 4(e). The same applies to the large-diameter optical fiber 3.

Figure 5A:
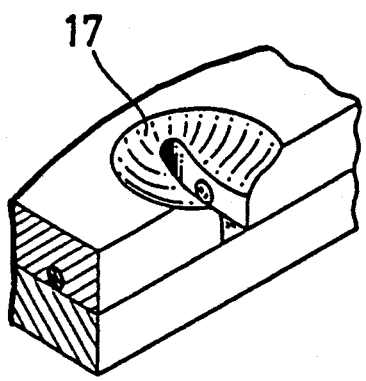
FIGS. 5(a and b) are perspective views showing examples of the aperture for admitting a test liquid.
Figure 5B:
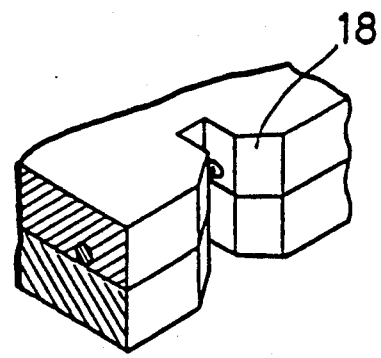

Referring to FIGS. 5(a) and 5(b) which show other examples of the aperture for admitting the test liquid in the detection means, FIG. 5(a) is relevant to the case wherein the center of the funnel-shaped opening 17 for admitting the test liquid is situated at a lateral side, while FIG. 5(b) is relevant to the case wherein the aperture is open in 3 directions, viz. on the near side and two lateral sides, with large chamferred portions 18 being formed at the near lateral sides. When the aperture is open on at least two sides in the above manner, the filling and removal of the test fluid are facilitated and as all the aperture portions other than these openings are closed, a measuring error due to infiltration of external light can be precluded.

The rod lens 2 and large-diameter glass optical fiber 3 juxtaposed with the narrow gap δ interposed as shown in FIG. 2 will be described in further detail. The rod lens 2 is a lens made of glass and configured in the shape of a rod. This lens is adapted to collimate the incident light from the plastic optical fiber into a light beam of substantially parallel rays. When the rod lens 2 is used on the light-receiving side, it converts a light beam of substantially parallel rays into an oblique beam for incidence on the glass optical fiber 3. The large-diameter glass optical fiber 3 is not a fine-gauge fiber with a diameter less than 0.5 mm, such as communication optical fiber, but is a fiber having a diameter of at least 0.5 mm. Since the narrow gap δ is approximately 1 mm, it is preferable to use a fiber with a diameter of about 1 mm and a length not less than 5 mm in order to minimize the reception loss or transmission loss of light. As to the combination of rod lens 2 and large-diameter glass optical fiber 3 defining the narrow gap δ, it may be the combination of 2 units of rod lens 2 or the combination of 2 units of large-diameter glass optical fiber 3.

However, different standards of measurement sensitivity should apply to the case in which the rod lens 2 is used on the light emission side and the case in which the large-diameter glass optical fiber 3 is used on the light emission side. Thus, the use of said rod lens 2 on both the light emission side and the light reception side is advantageous in that the emergent light is a beam of parallel rays as illustrated in FIGS. 8(a) and (b) and, hence, no loss of light occurs except the loss La or Ll due to the air or the test liquid in the narrow gap δ. When the large-diameter glass optical fiber is used on the light emission side, the following situation prevails. Namely, in the absence of the test liquid, since the refractive index of air in the narrow gap is smaller than the refractive index of optical glass fiber, a refraction loss Lout due to outward refraction occurs at the end face of the optical fiber except for the light emergent in parallel with the axis of the optical fiber as illustrated in FIG. 8(c). On the other hand, in the presence of the test liquid, the refractive index of which is generally larger than the refractive index of air, a larger amount of light is incident on the light reception side as shown in FIG. 8(d) and, hence, the refractive loss Lout is smaller that it is the case in the absence of the test liquid.

Therefore, in performing a determination, correction must be made for this situation. However, by selecting an appropriate glass material and making a necessary correction according to the test liquid, it is possible to use said large-diameter glass optical fiber on the light emission side and the fabrication cost of the detection means can be reduced as compared with the use of the rod lens.

Figure 6:
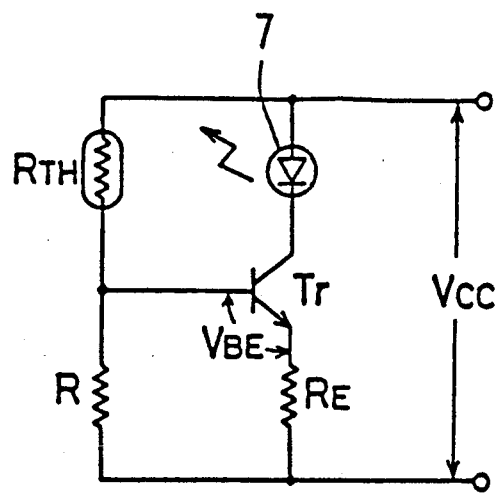
FIG. 6 is a circuit diagram relevant to an example of the driving circuit for a light-emitting element.

FIG. 6 is a circuit diagram relevant to an example of the driving circuit for the light-emitting element 7. In response to an input voltage Vcc, the light-emitting element 7 emits light but this emission of light is subject to the influence of ambient temperature. Therefore, a temperature-compensated circuit using a thermistar $R_{TH}$ and a transistor $T_r$, which takes advantage of the temperature characteristic of voltage $V_{BE}$, is employed.

Figure 7:
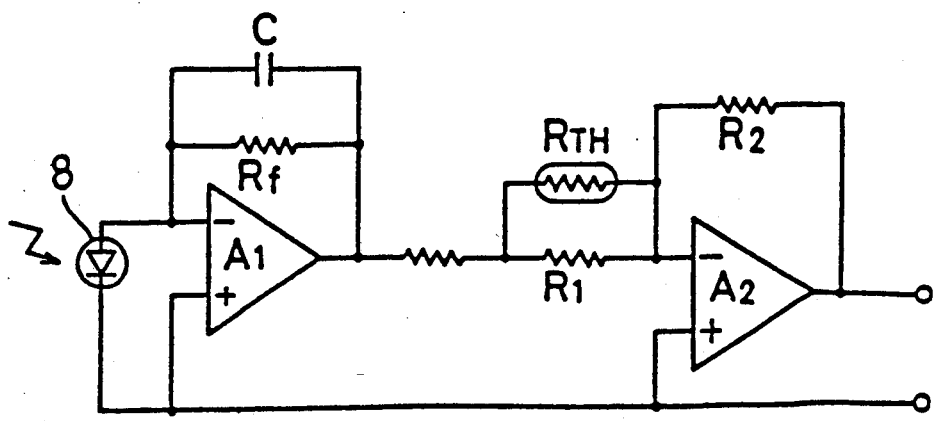
FIG. 7 is a circuit diagram relevant to an example of the amplifying circuit for the light-emitting element.

FIG. 7 is a circuit diagram showing an example of the amplifying circuit for the light-receiving element 8. While the output of the light-receiving element 8 is amplified by a preamplifing circuit comprised of an amplifier $A_1$, resistor $R_f$ and capacitor C, this preamplifying circuit is influenced by ambient temperature. Therefore, in this circuit, temperature compensation is effected by arranging an amplifier $A_2$ with a thermistar $R_{TH}$ and a resistor $R_1$ connected in parallel. The driving circuit and amplifying circuit shown in FIGS. 6 and 7 constitute parts of the measuring device body not shown or the optical liquid sensor as such. In this manner, the concentration of the liquid can be accurately measured with a simple circuit configuration, regardless of ambient temperature. Moreover, such simple driving and amplifying circuit configurations are made feasible because of the high measurement sensitivity of the system.

The above description is directed to the determination of the degree of contamination or concentration of the rest liquid. However, in the determination of the degree of degradation of engine oil, for instance, it is sometimes desirable to visually ascertain the degree of contamination and accumulate such empirical information for future use in addition to generating numerical data on light transmission loss. To meet this demand, an aperture for admitting the test liquid that allows visual inspection of the degree of contamination is shown in FIG. 9.

Referring to FIG. 9(a), a funnel-shaped aperture 20 for admitting the test liquid is coated, on its top side, with a white material 21 such as a white paint. Since the aperture portion for admitting the test liquid is generally made of an opaque material, engine oil or the like dripped into the aperture cannot be clearly ascertained due to interference by the color of the opaque material. However, when the aperture portion is coated with a white material 21, the degree of contamination of engine oil can be grossly ascertained with ease. As illustrated by the two-dot line in FIG. 9(a), a white marking 22 of, for example, a white paint, may be located near the funnel-shaped aperture 20 for admitting the test liquid. Thus, by dripping the engine oil onto this white marking as well as into the funnel-shaped aperture 20, the degree of contamination of the engine oil can be grossly evaluated.

In the arrangement illustrated in FIGS. 9(a), 9(b'), a transparent member is used in lieu of the white material. Thus, a transparent member 23 of, for example, glass is fitted into the bottom protective cover plate 5 in the position corresponding to the aperture for admitting the test liquid. As the engine oil or the like is dripped into an aperture 24, the clarity of the driped engine oil or the like can be directly ascertained grossly from below the transparent member 23.

The operation of the optical liquid sensor described above is explained below, referring to FIGS. 1, 2 and 8.

In the optical liquid sensor illustrated in FIG. 2, a mounting cap 19 at the end of the metallic flexible conduit 10 is connected to a measuring device body 20, which contains a system adapted to transform the light emission and reception outputs into light loss (dB) or liquid concentration data and record and display the data. As a predetermined amount of the liquid to be measured is dripped into the funnel-shaped aperture 15 shown in FIG. 1, the liquid fills up the narrow gap δ as shown in FIGS. 8(b) or (d) so that a light transmission loss proportional to the degree of fouling or concentration of the liquid takes place. The data is processed in the measuring device body to output the result. After completion of the determination, a breath can be blasted generally against the chamferred area 16 to blow out the test liquid from the narrow gap δ.

When the forward end of the rod lens and/or the large-diameter glass optical fiber is projecting by 0 to 0.3 mm as shown in FIG. 4, the drainage of the gap δ is more satisfactory and can be easily ascertained. Moreover, when said white material 21 or transparent member 23 is employed as shown in FIG. 9, the auxiliary gross observation of the degree of contamination or concentration can be accomplished.

The method for manufacturing the above optical liquid sensor, particularly one comprising a metal-sheathed rod lens and optical fiber assembly with said narrow gap interposed for measuring the light transmission loss is described below, referring to FIGS. 10 through 13.

First, the constructions of the metal sheath holder and the first and second adjusting jigs are described below, referring to FIGS. 12 and 13. Thereafter, manufacturing processes will be described, referring to FIGS. 10 10(a), (b), (b'), (c), (c'), (d) and (d') and FIGS. 11(a), (a'), (b) and (b') and 11. In FIGS. 12(a) and 12(b), a metal sheath holder 30 is a disk-shaped member with its top and bottom surfaces 30A, B being flat and parallel. The holder 30 is formed with a flat side surface 30C. Formed through the center of this disk is a metal sheath insertion hole 30D which is perpendicular to the bottom surface 30B. A threaded hole 30E opening to the metal sheath insertion hole 30D is tapped from the side peripheral surface of the disk and a set screw 31 is threaded into the hole 30E. This metal tube holder 30 is set on a platen and a metal sheath 25 is inserted into the metal tube insertion hole 30D until its lower end is abutted against the platen. Then, the set screw 31 is screwed in to secure the end of the metal sheath 25 in position where it does not protrude from the disk as shown. Referring to FIGS. 13(a) and 13(b), an adjusting jig 32 is a circular plate with its top and bottom surfaces 32A, B being flat and parallel. Perpendicularly drilled in the center of said flat plate is a threaded hole 32C. An adjusting rod 32D is vertically set in this threaded hole 32C and its height is set to H2. When the height of the rod lens 2 to be inserted into the metal sheath 25 is H4, the dimension H2+H4−H1 is set to a length which is amenable to coating with an adhesive composition. In addition to this first adjusting jig 32, a second adjusting jig 33 having a different height is also provided. Compared with the first adjusting jig 32, the adjusting rod 33D of this jig has a smaller height and the dimension H3+H4−H1 is set so that the leading end of the rod lens 2 protrudes slightly beyond or is flush with the metal sheath 25.

Referring, now, to FIGS. 10 10(a), (b), (b'), (c), (c'), (d) and (d') and FIGS. 11(a), (a'), (b) and (b') and 11, the process for inserting and securing the rod lens in position within the metal sheath is described below. As illustrated in FIG. 10(a), the metal sheath 25 is fixed to the metal sheath holder 30 (in the condition of FIG. 12) and the metal sheath 25 is fitted over the adjusting rod 32D of the first adjusting jig 32. In this manner, the metal sheath 25 is provided with a predetermined depth D as indicated in FIGS. 10(b)(b'). As shown in FIG. 10(c'), the rod lens 2 is inserted until its lower end is abutted against the tip of the adjusting rod 32D. The projecting length H5 of the rod lens 2 is just sufficient and appropriate for uniform coating with an adhesive composition 35 and not to allow excessive coating. The adhesive composition 35 is applied from the tip of a needle 34 while the metal sheath holder 30 is rotated (FIG. 10(c)). As shown in FIG. 10(d), the metal sheath holder 30 is then removed from the first adjusting jig 32 and placed recumbent on the platen by taking advantage of said flat surface 30C. While the rod lens 2 is forced into the metal sheath 25 by means of the needle 34, the superfluous adhesive composition is removed with the needle 34 (FIGS. 10(d),(d'). This operation is repeated until the leading end of the rod lens 2 advances to the position where it protrudes slightly beyond or becomes flush with the end face of the metal sheath 25. In this manner, the uniform application of the adhesive composition is made feasible without giving rise to rejects due to adhesion of the adhesive composition to the forward end of the rod lens because of excessive application or due to poor adhesion caused by a scarcity of the adhesive composition.

The procedure illustrated in FIGS. 11, 11(a), (a'), (b) and (b') is an alternative to the procedure of FIG. 10(d). As shown in FIG. 11(a), the metal sheath 25 held by the metal sheath holder 30 is slid over the first adjusting jig 32 to the second adjusting jig 33. While a distance of H6 is established between the rod lens 2 and the adjusting rod 33D, the distance of H5-H6 is set to 0 through 0.3 mm (FIG. 11(a')). Referring to FIGS. 11(b), (b'), the rod lens 2 is forced in with the needle 34 and the excess adhesive 35 is removed with the needle as the metal sheath holder 30 is rotated. This procedure is repeated until the lower end of the rod lens 2 is abutted against the forward end of the adjusting rod 33D. By this manufacturing method, the forward end of the rod end 2 can be allowed to protrude by 0 to 0.3 mm from the metal sheath 25 with good dimensional reproducibility.

By the above procedure, there can be obtained a rod lens snugly accommodated in a metal sheath as illustrated in FIG. 4(b) or (c). The large-diameter glass optical fiber can also be inserted into the metal sheath in the same manner.

Referring, now, to FIGS. 14(a)-(c) through 18, an automotive oil/battery checker implemented using the above-described optical liquid sensor is described below. In these views, the members corresponding to those indicated in FIGS. 1 through 4 are designated by the numerals greater than the corresponding numerals used in the latter views by 100.

As shown in FIGS. 14(a)-(c) and 15, the oil/battery checker comprises a sensor head 100, a flexible tube 110' and a measuring unit 120.

Since the sensor head 100 is similar in construction to the sensor illustrated in FIGS. 1 through 4, any overlapping description is omitted.

At the forward end of the sensor head 100, a generally bracket-shaped terminal 141 made of an electrically-conductive material, such as brass, is rigidly secured to a top protective cover plate 104 with an adhesive or the like and a lead wire 142a and a resistor 143, both of which are connected to this terminal 141, are disposed in the protective cover plates 104 and 105. The lead wire 142a passes over the plastic optical fiber 101 and through the resistor 143 accommodated in a space 144 and extends along the plastic optical fiber 101. This lead wire 142a is an insulated twisted-wire conductor and the insulator cladding preferably is heat- and oil-resistant and has satisfactory mechanical properties. The resistor 143 may be installed in the measuring unit 120.

The underside of the bottom protective cover plate 105 is flat and a magnetic plate 146 is embedded flush in the approximate center of said plate 105.

In this checker, the part indicated at 125 is an aperture for admitting oil and the degree of contamination of oil is determined by dripping the oil into this aperture.

While the rod lens 102 is disposed directly in a groove 106 in this embodiment, too, it may be accommodated through a metallic sheath 125 like that shown in FIG. 4.

Figure 16A:
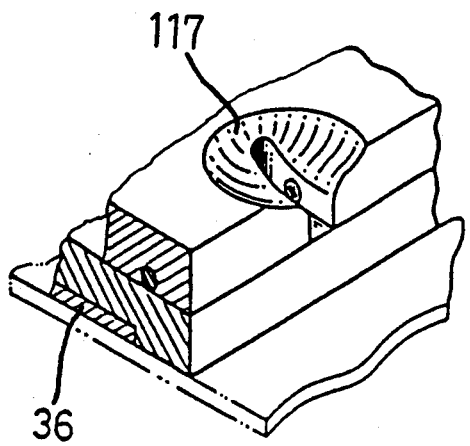
FIGS. 16(a,b) are perspective views showing other examples of the aperture for admitting engine oil.
Figure 16B:
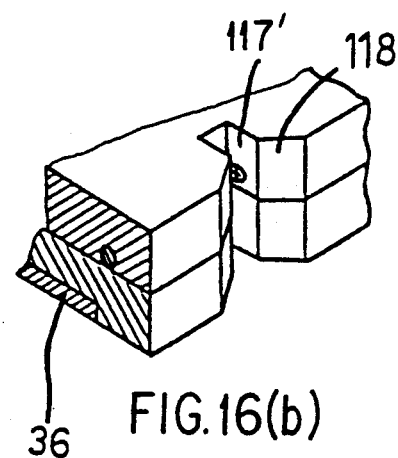

FIGS. 16(a) and 16(b) other examples of the aperture for admitting engine oil. Excepting a magnetic plate 146, the construction is identical with that shown in FIG. 5. With regard to the manner of dripping oil into openings 117,117' for admitting oil, the sensor head 100 is attached to a suitable horizontal location near the engine of the car by utilizing the magnetic plate 146. Then, the oil can be conveniently dripped with a single hand, while the other hand is used to manipulate the measuring unit 120, for instance.

Figure 17A:
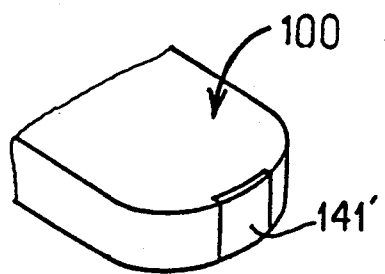
FIGS. 17(a,b) are perspective views showing other examples of the manner of mounting a terminal for detecting the battery charge voltage.
Figure 17B:
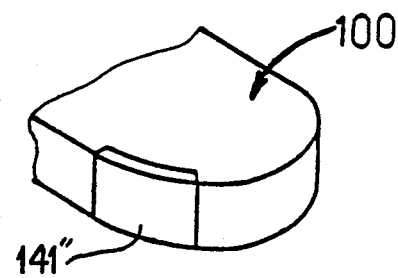
Figure 18:
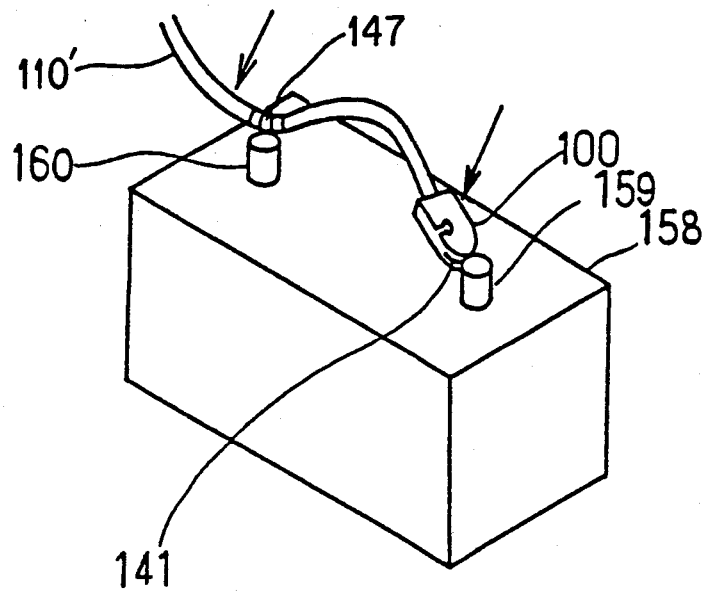
FIG. 18 is a perspective view showing an example of operation of the automotive oil/battery checker.
Figure 19:
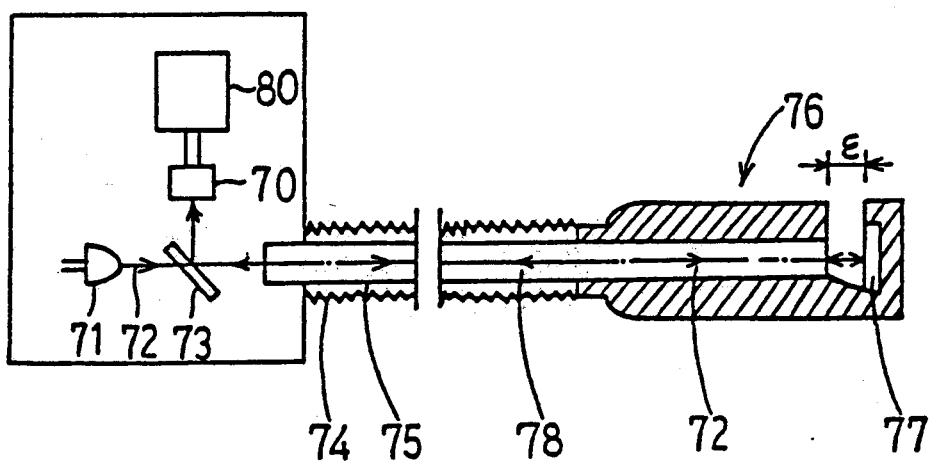
FIG. 19 is a diagrammatic view showing the prior art optical liquid sensor.

FIGS. 17(a) and 17(b) show other examples of the above-mentioned terminal. Thus, it may be a terminal 141' affixed to the forward flattened surface of the sensor head 100 as shown in FIG. 17(a) or may be a terminal 141" affixed to one lateral side of the sensor head 100 as shown in FIG. 17(b). Thus, the terminal can be attached to an optical location according the configuration of the sensor head 100 and/or the configuration of the battery.

Referring, now, to FIGS. 14(a)-(c) and 15, a flexible conduit 110' consists of a metallic flexible tube 110 and a plastic cladding 148 and is highly flexible. Disposed partway is a cylindrical member 149 made of, for example, a polycarbonate resin. A ring terminal 147 made of an electrically conductive material, such as brass, is rigidly secured centrally to this cylindrical member 149. This ring terminal 147 and the aforementioned terminal 141 form a couple and the distance L between these two terminals is longer than the distance between the power terminals of the battery. The lead wire 142b connected to the ring terminal 147 extends along the plastic optical fibers 101a and 101b. Thus, the plastic optical fibers 101a and 101b and lead wires 142a and 142b are collectively accommodated in the flexible tube 110'. The joint between the sensor head 100 and the flexible tube 110' is sealed with an adhesive 111.

Referring, now to FIG. 15, the measuring unit 120 is described in detail below. A connector 151 of the measuring unit 120 is such that the cores of the plastic optical fibers 101a and 101b and lead wires 142a and 142b in the flexible conduit 110' can be connected in one operation. Built into this measuring unit 120 are a voltmeter 153 having a built-in power source 152, a light-emitting segment 107 and a light-receiving segment 108. The voltmeter 153 can be a commercial product.

An example of the driving circuit for the light-emitting segment 107 is shown in FIG. 6, while an example of the amplifying circuit for the light-receiving segment 108 is shown in FIG. 7. The above driving circuit and amplifying circuit are disposed within the measuring unit or the sensor head 100. In this arrangement, the degree of contamination of the engine oil can be accurately determined regardless of ambient temperature.

The operation of the automotive oil/battery checker described above is explained below, referring to FIGS. 14(a)-(c), 15 and 18.

In the automotive oil/battery checker illustrated in FIG. 15, the terminal end of the flexible tube 110' is connected to the measuring unit 120 via the connector 151'. The measuring unit 120 contains a device adapted to measure the light emission and light reception powers and convert the light loss (dB) value to the degree of contamination and indicate or print the result of conversion and a device for displaying or printing voltage readings. For the inspection of engine oil in regard to the degree of contamination, the sensor head 100 is attached to a suitable horizontal location within the engine compartment by utilizing the magnetic plate 146 illustrated in FIG. 14(a). Then, a predetermined quantity of the oil to be measured is filled into the aperture 125 for admitting the oil, whereupon the narrow gap δ is filled up with the oil and, as a consequence, a transmission loss of light proportional to the degree of fouling of the oil takes place. The degree of contamination is assessed by processing the data in the measuring unit Furthermore, more, when the white material 21, 22 as shown in FIG. 9(a) or transparent member 23 as shown in FIGS. 9(b), (b'), the degree of fouling or concentration of the liquid can be ascertained by direct visual inspection as an adjunctive measure. In this connection, the measuring unit 120 can be hung in a suitable position near the engine so that such direct observation can be made offhand. After determination, a breath is blasted against the chamferred area 116 to blow off the oil from the narrow gap δ. When the forward end of the rod lens and/or the large-diameter glass optical fiber is projecting by 0 to 0.3 mm as shown in FIG. 4, a good drainage of the narrow gap δ can be assured and can also be visually confirmed easily. Moreover, when the charge voltage of the battery is to be checked, the sensor head 100 and the portion near the ring terminal 147 of the flexible sheath 110' are held by hand and the terminal 141 and ring terminal 147 are contacted to the power terminals 159 and 160 of the battery 158 as indicated by the arrowmarks in FIG. 18. Then, the voltmeter of the measuring unit 120 hung in a suitable position is read. Thus, by conducting the above procedures in succession, the degree of contamination of the engine oil and the charge voltage of the battery can be conveniently inspected. The order of the test for the degree of contamination of engine oil and the battery charge voltage test is optional.

In the optical liquid sensor of the invention wherein a detection means is disposed with a narrow gap interposed in a linear portion of a folded-back portion of the optical fiber, the loss of light at the gap due to offset of the light path is minimized. Furthermore, the rod lens and/or large-diameter glass optical fiber is chemically stable against a broad variety of liquids to be tested, thus contributing to reduction in the loss of light at the narrow gap.

In the method of manufacturing an optical liquid sensor according to the present invention, wherein the rod lens or the large-diameter glass optical fiber is caused to protrude from the metal sheath by a predetermined length and be supported from below, no variation occurs in the length of projection. Therefore, the adhesive can be easily and uniformly applied and accordingly the incidence of rejects is minimized.

With the automotive oil/battery checker according to the present invention, both the assessment of the degree of contamination of engine oil and the detection of battery charge voltage can be accomplished with a single measuring apparatus so that the two tests can be rapidly carried out.

We claim:
1. An automotive oil/battery checker comprising
   a sensor head comprising a folded-back light transmission path which is hermetically closed except at a narrow gap provided in one location in the folded-back portion of said path for admitting an oil to be tested for contamination and one terminal disposed on the surface thereof for detecting a battery charge voltage,
   a flexible conduit disposed adjacent to said sensor head and, covering both an outward segment and an inward segment of said light transmission path, having another terminal disposed on the surface thereof for detecting a battery charge voltage, and further covering lead wires connected to said two terminals, and
   a measuring unit disposed at a terminal end of said flexible conduit and having a light loss detector having a light emission means and a light reception means and a voltmeter connected to said two terminals through lead wires,
   the distance between one of said terminals which is disposed on said sensor head and the other terminal disposed on said flexible conduit being larger than the distance between two power terminals of a battery and being adjustable in response to flexure of said flexible conduit, whereby both the detection of the degree of degradation of oil and the detection of battery charge voltage can be effected.

2. An automotive oil/battery checker according to claim 1 wherein a magnetic plate is flush-mounted on the surface of said sensor head which is opposite to the aperture of said narrow gap for admitting engine oil.

3. An automotive oil/battery checker according to claim 1 further comprising a detection means comprising a pair of units of a rod lens and/or a large-diameter glass optical fiber and wherein said narrow gap is formed by inserting each rod lens and/or large-diameter glass optical fiber forming said pair in a metal sheath with its forward end projecting beyond the sheath by 0 to 0.3 mm with the other end abutted against the core of an optical fiber in said metal sheath so that two projecting ends of the pair are juxtaposed in the metal sheath.

4. An automotive oil/battery checker according to claim 1 wherein a covering member sealing the folded-back portion is made of a light-opaque material and the aperture for admitting engine oil is open on at least two of its four sides.

5. An automotive oil/battery checker according to claim 4 wherein the aperture portion around said narrow gap is partially formed in a funnel-like configuration.

6. An automotive oil/battery checker according to claim 1 wherein the top side or adjoining region of the aperture for admitting engine oil into said narrow gap is comprised of a white material.

7. An automotive oil/battery checker according to claim 1 wherein the underside of said aperture for admitting engine oil into said narrow gap is comprised of a light-transparent material such as glass.

8. An optical liquid sensor comprising an optical fiber folded black in two, a light-emitting element disposed at one end of said optical fiber, a light-receiving element disposed at the other end, and a detection means comprising a pair of units of a rod lens and/or a large-diameter glass optical fiber with a narrow gap interposed therebetween in a linear segment of a folded back portion of said optical fiber, said folded-back portion being hermetically sealed except at an aperture portion for admitting a liquid to be tested into said narrow gap, each rod lens and/or said large-diameter glass optical fiber forming said pair being accommodated in a metal sheath with its forward end projecting beyond the end face of said metal sheath by 0 to 0.3 mm and with the other end being abutted against the core of said optical fiber in said metal sheath, the projecting ends of said pair being juxtaposed with said narrow gap interposed therebetween.

9. An optical liquid sensor comprising an optical fiber folded back in two, a light-emitting element disposed at one end of said optical fiber, a light-receiving element disposed at the other end, and a detection means comprising a pair of units of a rod lens and/or a large-diameter glass optical fiber with a narrow gap interposed therebetween in a linear segment of a folded back portion of said optical fiber, said folded-back portion being hermetically sealed except at an aperture portion for admitting a liquid to be tested into said narrow gap, said hermetical sealing being effected by a light-opaque member and said aperture portion for admitting the liquid to be tested being open only on upper and outer lateral sides thereof.

10. An optical liquid sensor according to claim 9 wherein said aperture portion around said narrow gap is partially formed in a funnel-like configuration.

11. An optical liquid sensor comprising an optical fiber folded back in two, a light-emitting element disposed at one end of said optical fiber, a light-receiving element disposed at the other end, and a detection means comprising a pair of units of a rod lens and/or a large-diameter glass optical fiber with a narrow gap interposed therebetween in a linear segment of a folded back portion of said optical fiber, said folded-back portion being hermetically sealed except at an aperture portion for admitting a liquid to be tested into said narrow gap, said aperture portion around said narrow gap or a region adjacent thereto being comprised of a white material.

12. An optical liquid sensor according to claim 11 wherein said aperture portion around said narrow gap is partially formed in a funnel-like configuration.

13. An optical liquid sensor comprising an optical fiber folded back in two, a light-emitting element disposed at one end of said optical fiber, a light-receiving element disposed at the other end, and a detection means comprising a pair of units of a rod lens and/or a large-diameter glass optical fiber with a narrow gap interposed therebetween in a linear segment of a folded back portion of said optical fiber, said folded-back portion being hermetically sealed except at an aperture portion for admitting a liquid to be tested into said narrow gap, a part of said detection means lying immediately under said aperture being comprised of a light-transparent material.

* * * * *